(12) United States Patent
Tian et al.

(10) Patent No.: US 11,771,336 B2
(45) Date of Patent: Oct. 3, 2023

(54) NON-UNIFORM EXCITATION FIELD-BASED METHOD AND SYSTEM FOR PERFORMING MAGNETIC NANOPARTICLE IMAGING

(71) Applicant: INSTITUTE OF AUTOMATION, CHINESE ACADEMY OF SCIENCES, Beijing (CN)

(72) Inventors: Jie Tian, Beijing (CN); Yanjun Liu, Beijing (CN); Hui Hui, Beijing (CN); Lin Yin, Beijing (CN); Xin Feng, Beijing (CN)

(73) Assignee: Institute Of Automation, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/811,235

(22) Filed: Jul. 7, 2022

(65) Prior Publication Data

US 2023/0094291 A1 Mar. 30, 2023

(30) Foreign Application Priority Data

Sep. 23, 2021 (CN) .......................... 202111125585.6

(51) Int. Cl.
*A61B 5/0515* (2021.01)
*G01R 33/54* (2006.01)

(52) U.S. Cl.
CPC ............ *A61B 5/0515* (2013.01); *G01R 33/54* (2013.01)

(58) Field of Classification Search
None
See application file for complete search history.

(56) References Cited

U.S. PATENT DOCUMENTS

2006/0273792 A1 12/2006 Kholmovski et al.
2011/0221438 A1 9/2011 Goodwill et al.
(Continued)

FOREIGN PATENT DOCUMENTS

CN 110051352 A 7/2019
WO WO-2005121838 A2 12/2005
(Continued)

OTHER PUBLICATIONS

"Chinese Application Serial No. 202111125585.6, Notification to Grant dated Sep. 2, 2022", w/ English Translation, (Sep. 2, 2022), 4 pgs.
(Continued)

*Primary Examiner* — Jay Patidar
(74) *Attorney, Agent, or Firm* — Schwegman Lundberg & Woessner, P.A.

(57) ABSTRACT

The present disclosure belongs to a field of biomedical imaging technology, and in particularly to a non-uniform excitation field-based method and system for performing a magnetic nanoparticle imaging. The present disclosure includes: separating the non-uniform excitation field into independent space and current time functions by a spatialtemporal separation method; calculating a normalized signal peak through the current time function; constructing a reconstruction mathematical model based on the normalized signal peak and an imaging subunit volume; and quantitatively reconstructing a spatial distribution of a nanoparticle by combining the normalized signal peak, a non-uniform spatial function of the excitation field and the reconstruction mathematical model, so as to achieve the magnetic nanoparticle imaging of a to-be-reconstructed object.

10 Claims, 2 Drawing Sheets

(56) References Cited

U.S. PATENT DOCUMENTS

| | | |
|---|---|---|
| 2015/0071514 A1 | 3/2015 | Wang et al. |
| 2015/0372687 A1 | 12/2015 | Buhrman et al. |
| 2018/0303373 A1 | 10/2018 | Freeman et al. |
| 2020/0003856 A1 | 1/2020 | Constable et al. |
| 2020/0245893 A1* | 8/2020 | Goodwill ............... G01N 27/72 |

FOREIGN PATENT DOCUMENTS

| | | |
|---|---|---|
| WO | WO-2011121511 A1 | 10/2011 |
| WO | WO-2020235505 A1 | 11/2020 |

OTHER PUBLICATIONS

"Chinese Application Serial No. 202111125585.6, Office Action dated Jan. 19, 2022", w/ English Translation, (Jan. 19, 2022), 12 pgs.

Top, Can Baris, et al., "Trajectory analysis for field free line magnetic particle imaging", Medical Physics 46.4, (2019), 1592-1607.

\* cited by examiner

A spatiotemporal separation processing is performed on a non-uniform excitation field $H_E(r,t)$, so that the non-uniform excitation field is divided into an independent spatial function $A_0(r)$ and an independent time function $I_E(t)$, that is, $H_E(r,t) = A_0(r)I_E(t)$ A sensitivity spatial function $p_R(r)$ of a receiving coil is acquired An excitation current $I_E(t)$ is introduced into an excitation coil to generate a required non-uniform excitation field in an imaging space, so as to excite a magnetic nanoparticle in a space A magnetic nanoparticle response voltage signal $u_p(t)$ is detected using a receiving coil in real time, and then a normalized magnetic nanoparticle signal $s(t) = u_p(t)/[I_E(t)]^k$ is calculated A gridding processing is performed on an imaging space to be divided into $N$ imaging subunits A peak $s_p$ of the normalized magnetic nanoparticle signal $s(t)$ is calculated A reconstruction equation of the normalized signal peak $s_p$ and a magnetic nanoparticle spatial distribution $c(r_n)$ is established The nanoparticle spatial distribution $c(r_n)$ is reconstructed using the above equation and the the normalized signal peak $s_p$, so as to achieve a magnetic nanoparticle imaging of a to-be-reconstructed object

NON-UNIFORM EXCITATION FIELD-BASED METHOD AND SYSTEM FOR PERFORMING MAGNETIC NANOPARTICLE IMAGING

CROSS-REFERENCE TO RELATED APPLICATION

This application claims the priority of Chinese Patent Application No. 202111125585.6 filed on Sep. 23, 2021 in the China National Intellectual Property Administration, the content of which is incorporated herein by reference in entirety.

TECHNICAL FIELD

The present disclosure relates to a field of a biomedical imaging technology, and particularly to a non-uniform excitation field-based method and system for performing a magnetic nanoparticle imaging.

BACKGROUND

A magnetic nanoparticle is a nanoscale particle with superparamagnetism. In recent years, the magnetic nanoparticle has been widely researched and applied as a novel medical imaging tracer in clinical problems such as tumor detection, magnetic particle thermotherapy, targeted drug delivery and the like.

The method for performing a magnetic nanoparticle imaging (MPI) includes controlling a gradient magnetic field with a high field strength to code an entire imaging field, applying a high-frequency uniform excitation field to excite the magnetic nanoparticle to generate a nonlinear response, and finally performing an imaging by using a response voltage signal detected by a receiving coil. A traditional magnetic nanoparticle imaging uses a uniform excitation field, which is intended to establish a one-to-one mapping relationship between a detection voltage signal time sequence u(t) and a magnetic nanoparticle spatial distribution c(r). The one-to-one mapping relationship is shown in the following equation.

$$u(t) = -\mu_0 \int_V \frac{\partial M_0[H_E(r, t)]}{\partial t} p_R(r)c(r)dV$$

In practice, it is very difficult to generate a wide-range uniform magnetic field. Generally, a volume of an excitation coil needs to be increased to acquire a larger uniform range, which may cause problems such as a high power consumption, a serious heat generation and the like. At present, an existing commercial magnetic nanoparticle imaging device is only suitable for an imaging of a small animal, and a length and a width of an imaging field of view may only be about a few centimeters.

Therefore, in order to further promote a development of a magnetic nanoparticle imaging technology to a large animal and a clinical field, a novel magnetic nanoparticle imaging method capable of overcoming a limitation of a uniform magnetic field excitation is still urgently required in the art.

SUMMARY

In order to solve the above-mentioned problem in the prior art, that is, the problem that the prior art may not overcome a limitation of the uniform magnetic field excitation, resulting in a small imaging field of view and a limited application range of the magnetic nanoparticle, the present disclosure provides a non-uniform excitation field-based method for performing a magnetic nanoparticle imaging, including:

exciting a to-be-reconstructed object through a non-uniform excitation field $H_E(r, t)$, and performing a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;

acquiring, based on the spatial distribution $A_0(r)$ of the non-uniform magnetic field generated by the excitation coil and the excitation current time-domain waveform $I_E(t)$, a magnetic field space distribution $p_R(r)$ generated by a receiving coil and a magnetic nanoparticle response voltage signal $u_p(t)$;

performing a normalization processing on the magnetic nanoparticle response voltage signal $u_p(t)$, so as to obtain a normalized magnetic nanoparticle signal s(t);

performing a gridding processing on an imaging space of the to-be-reconstructed object, so as to obtain N imaging subunits, wherein a n-th imaging subunit has a volume $\Delta V_n$ and n=1, 2, ..., N;

calculating a normalized signal peak $s_p$ based on the normalized magnetic nanoparticle signal s(t), and constructing a first mathematical model between the normalized signal peak $s_p$ and a magnetic nanoparticle spatial distribution $c(r_n)$ by combining the volume $\Delta V_n$ of the imaging subunit; and solving the first mathematical model to obtain the magnetic nanoparticle spatial distribution $c(r_n)$, so as to achieve the magnetic nanoparticle imaging of the to-be-reconstructed object.

In some embodiments, the excitation current time-domain waveform $A_0(r)$ of the non-uniform magnetic field generated by the excitation coil and the magnetic field space distribution $p_R(r)$ generated by the receiving coil are acquired by one of an actual measurement method, an analytical equation solution method or a finite element numerical simulation method, respectively.

In some embodiments, the excitation current time-domain waveform $I_E(t)$ is one of a sine wave, a cosine wave, a square wave or a pulse wave.

In some embodiments, the normalized magnetic nanoparticle signal s(t) is acquired by:

$$s(t)=u_p(t)/[I_E(t)]^k$$

wherein k is a frequency multiplication number of the magnetic nanoparticle response voltage signal $u_p(t)$, and k is a positive odd number.

In some embodiments, the first mathematical model between the normalized signal peak $s_p$ and the magnetic nanoparticle spatial distribution $c(r_n)$ is expressed as:

$$s_p = \gamma \sum_{n=1}^{N} [A_0(r_n)]^k p_R(r_n)c(r_n)\Delta V_n$$

wherein $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, ..., N and n represents the n-th imaging subunit of N imaging subunits, and γ represents a proportionality constant related to a frequency of an excitation field, a magnetic moment of a single magnetic particle and a temperature.

In another aspect of the present disclosure, there is provided a spatialtemporally coded non-uniform excitation field-based method for performing a magnetic nanoparticle imaging, including:

generating, on the basis of exciting a to-be-reconstructed object through a non-uniform excitation field $H_E(r, t)$ of the above-mentioned method, a gradient magnetic field with a field-free region in an imaging space through a pair of direct current coils in an opposite axial direction or a permanent magnet;

changing a distribution of the gradient magnetic field through a low-frequency alternating magnetic field generated by a low-frequency alternating current coil, and driving the field-free region to scan and traverse an entire imaging space along a set track, so as to obtain M scanning moments and M scanning positions;

acquiring a normalized signal peak $s_p(t_m)$ at a m-th moment thorough the above-mentioned method, wherein m=1, 2, . . . , M;

acquiring a voxel function $\Delta V(t_m, r_n)$ of a response voltage signal of a n-th imaging subunit at a m-th scanning moment according to the distribution of the gradient magnetic field and the scanned track;

constructing a second mathematical model between the normalized signal peak $s_p(t_m)$ and a magnetic nanoparticle spatial distribution $c(r_n)$ based on the normalized signal peak $s_p(t_m)$ at the m-th moment and the voxel function $\Delta V(t_m, r_n)$ of the response voltage signal at the m-th scanning moment; and solving the second mathematical model to obtain the magnetic nanoparticle spatial distribution $c(r_n)$, so as to achieve the magnetic nanoparticle imaging of the to-be-reconstructed object.

In some embodiments, the second mathematical model between the normalized signal peak $s_p(t_m)$ and the magnetic nanoparticle spatial distribution $c(r_n)$ is expressed as:

$$s_p(t_m) = \gamma \sum_{n=1}^{N} [A_0(r_n)]^k p_R(r_n) c(r_n) \Delta V(t_m, r_n)$$

wherein $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, . . . , N represents the n-th imaging subunit of N imaging subunits, and γ represents a proportionality constant related to a frequency of an excitation field, a magnetic moment of a single magnetic particle and a temperature.

In a third aspect of the present disclosure, a non-uniform excitation field of a coil array-based method for performing a magnetic nanoparticle imaging is provided, including:

sequentially exciting, on the basis of exciting a to-be-reconstructed object through a non-uniform excitation field $H_E(r, t)$ of the above-mentioned method, an imaging space by using a plurality of excitation coils with same or different axial directions at different positions, so as to construct an excitation coil array;

simultaneously detecting a magnetic nanoparticle response voltage signal by using a plurality of receiving coils with same or different axial directions at different positions so as to construct a receiving coil array, wherein the plurality of receiving coils correspond to the plurality of excitation coils;

acquiring a unit current magnetic field spatial function $A_0^m(r_n)$ of a m-th excitation coil and a sensitivity spatial function $p_R^l(r_n)$ of a l-th receiving coil, acquiring a volume $\Delta V_n$ of a n-th imaging subunit and n=1, 2, . . . , N, performing a normalization of a m×l magnetic nanoparticle response voltage signal $u_p(t)$, and acquiring a normalized signal peak $s_p^{m \times l}$ of a normalized magnetic nanoparticle signal s(t) through the above-mentioned method;

constructing a third mathematical model between the normalized signal peak $s_p^{m \times l}$ and a magnetic nanoparticle spatial distribution $c(r_n)$ based on the normalized signal peak $s_p^{m \times l}$ and the volume $\Delta V_n$ of the imaging subunit; and solving the third mathematical model to acquire the magnetic nanoparticle spatial distribution $c(r_n)$, so as to achieve the magnetic nanoparticle imaging of the to-be-reconstructed object.

In some embodiments, the third mathematical model between the normalized signal peak $s_p^{m \times l}$ and the magnetic nanoparticle spatial distribution $c(r_n)$ is expressed as:

$$s_p^{m \times l} = \gamma \sum_{n=1}^{N} [A_0^m(r_n)]^k p_R^l(r_n) c(r_n) \Delta V_n$$

wherein $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, . . . , N and n represents the n-th imaging subunit of N imaging subunits, γ represents a proportionality constant related to a frequency of an excitation field, a magnetic moment of a single magnetic particle and a temperature, m represents the m-th excitation coil and l represents the l-th receiving coil.

In a fourth aspect of the present disclosure, there is provided a non-uniform excitation field-based system of performing a magnetic nanoparticle imaging, including:

a first magnetic field excitation module configured to excite a to-be-reconstructed object through a non-uniform excitation field $H_E(r, t)$;

a spatialtemporal separation module configured to perform a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;

a magnetic field spatial distribution and response voltage signal acquisition module configured to acquire, based on the spatial distribution $A_0(r)$ of the non-uniform magnetic field generated by the excitation coil and the excitation current time-domain waveform $I_E(t)$ a magnetic field space distribution $p_R(r)$ generated by a receiving coil and a magnetic nanoparticle response voltage signal $u_p(t)$;

a normalization module configured to perform a normalization processing on the magnetic nanoparticle response voltage signal $u_p(t)$, so as to obtain a normalized magnetic nanoparticle signal s(t);

a gridding module configured to perform a gridding processing on an imaging space of the to-be-reconstructed object, so as to obtain N imaging subunits, wherein a n-th imaging subunit has a volume $\Delta V_n$ and n=1, 2, . . . , N;

a first model construction module configured to calculate a normalized signal peak $s_p$ based on the normalized magnetic nanoparticle signal s(t) and to construct a first mathematical model between the normalized signal peak $s_p$ and the magnetic nanoparticle spatial distribution $c(r_n)$ by combining the volume $\Delta V_n$ of the imaging subunit; and a first imaging module configured to solve the first mathematical model to obtain the magnetic nanoparticle spatial distribution $c(r_n)$, so as to achieve the magnetic nanoparticle imaging of the to-be-reconstructed object.

BRIEF DESCRIPTION OF THE DRAWINGS

The other features, objects and advantages of the present disclosure will be clearer by reading the detailed description of non-limiting embodiments made with reference to the following accompanying drawings.

DETAILED DESCRIPTION OF EMBODIMENTS

The present disclosure will be further described in detail with reference to the accompanying drawings and examples. It may be understood that the specific embodiments described herein are merely illustrative of the present disclosure and are not intended to limit the scope of the present disclosure. In addition, it should be noted that, for convenience of description, only portions related to the present disclosure are illustrated in the accompanying drawings.

It should be noted that, embodiments and features of the embodiments in the present disclosure may be combined with each other without a conflict. The present disclosure will be described in detail below with reference to the accompanying drawings in conjunction with the embodiments.

In the present disclosure, a non-uniform excitation field-based method for performing a magnetic nanoparticle imaging is provided, including:

step S10 of exciting a to-be-reconstructed object through a non-uniform excitation field $H_E(r, t)$, and performing a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;

step S20 of acquiring, based on the spatial distribution $A_0(r)$ of the non-uniform magnetic field generated by the excitation coil and the excitation current time-domain waveform $I_E(t)$, a magnetic field space distribution $p_R(r)$ generated by a receiving coil and a magnetic nanoparticle response voltage signal $u_p(t)$;

step S30 of performing a normalization processing on the magnetic nanoparticle response voltage signal $u_p(t)$, so as to obtain a normalized magnetic nanoparticle signal s(t);

step S40 of performing a gridding processing on an imaging space of the to-be-reconstructed object, so as to obtain N imaging subunits, wherein a n-th imaging subunit has a volume $\Delta V_n$ and n=1, 2, . . . , N;

step S50 of calculating a normalized signal peak $s_p$ based on the normalized magnetic nanoparticle signal s(t), and constructing a first mathematical model between the normalized signal peak $s_p$ and a magnetic nanoparticle spatial distribution $c(r_n)$ by combining the volume $\Delta V_n$ of the imaging subunit; and step S60 of solving the first mathematical model to obtain the magnetic nanoparticle spatial distribution $c(r_n)$, so as to achieve the magnetic nanoparticle imaging of the to-be-reconstructed object.

Figure 1:
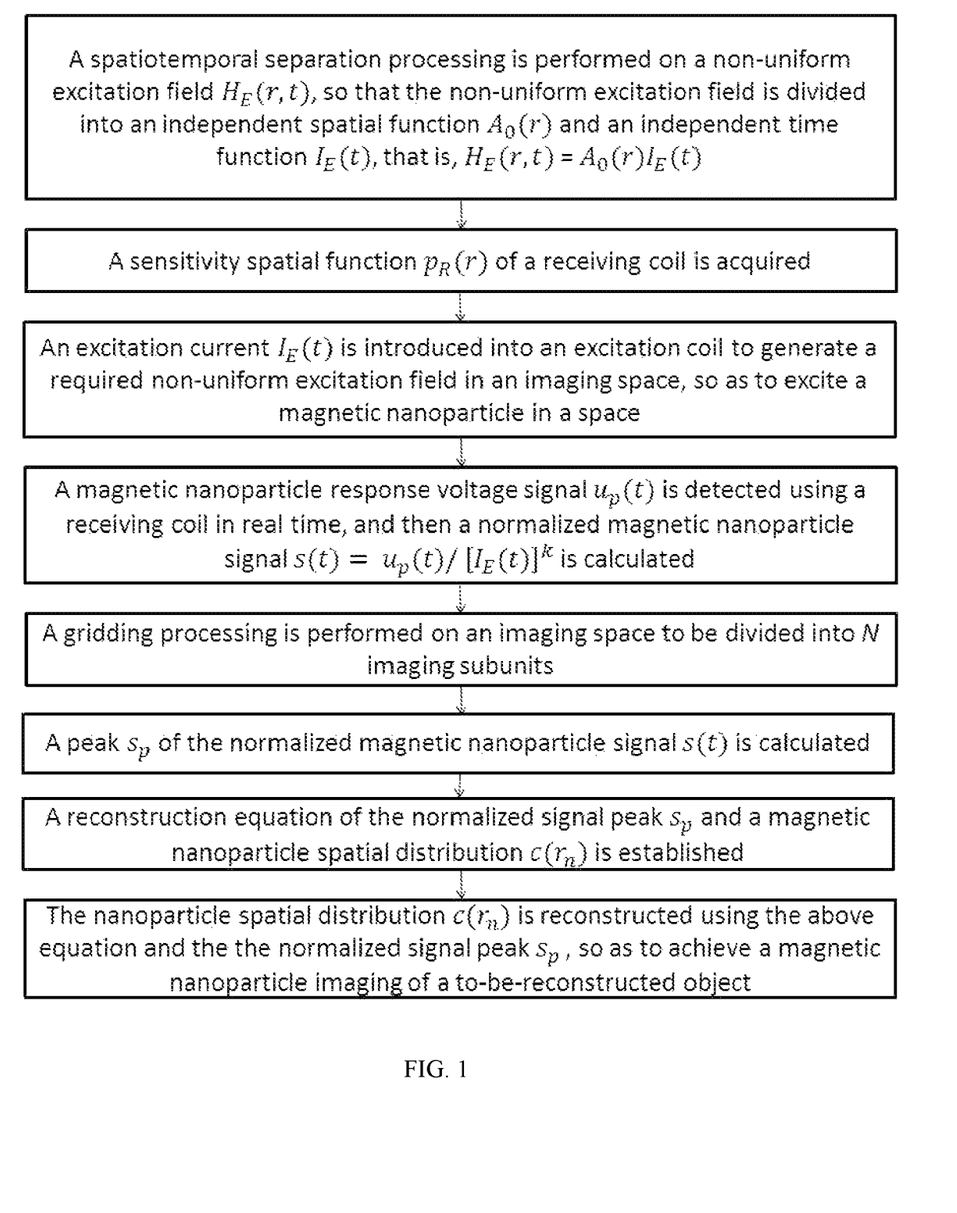
FIG. 1 shows a schematic flow diagram of a non-uniform excitation field-based method for performing a magnetic nanoparticle imaging according to the present disclosure.

In order to more clearly describe the non-uniform excitation field-based method for performing a magnetic nanoparticle imaging according to the present disclosure, the steps in the embodiments of the present disclosure will be described below in detail with reference to FIG. 1.

In a first embodiment of the present disclosure, the non-uniform excitation field-based method for performing a magnetic nanoparticle imaging includes step S10 to step S60. The steps are described in detail as follows.

In the step S10, a to-be-reconstructed object is excited through a non-uniform excitation field $H_E(r, t)$, and a spatialtemporal separation for the non-uniform excitation field $H_E(r, t)$ is performed, so as to obtain a spatial distribution $A_0(r)$ of a non-uniform magnetic field generated by an excitation coil and an excitation current time-domain waveform $I_E(t)$.

The spatial distribution $A_0(r)$ of the non-uniform magnetic field generated by the excitation coil and the excitation current time-domain waveform $I_E(t)$ are an independent spatial function and an independent time function, respectively. $A_0(r)$ may be acquired by a method such as an actual measurement method, an analytical equation solution method or a finite element numerical simulation method, etc. $I_E(t)$ may be mainly generated by a signal generator and a power amplifier without a limitation on a waveform, and may be a sine wave, a cosine wave, a square wave or a pulse wave, etc.

A relationship between the non-uniform excitation field $H_E(r, t)$ and the spatial distribution $A_0(r)$ of the non-uniform magnetic field generated by the excitation coil and the excitation current time-domain waveform $I_E(t)$ is shown in equation (1).

$$H_E(r,t)=A_0(r)I_E(t) \qquad (1)$$

In the step S20, a magnetic field spatial distribution $p_R(r)$ generated by a receiving coil and a magnetic nanoparticle response voltage signal $u_p(t)$ are acquired based on the spatial distribution $A_0(r)$ of the non-uniform magnetic field generated by the excitation coil and the excitation current time-domain waveform $I_E(t)$.

A sensitivity spatial function of the receiving coil, i.e., the magnetic field spatial distribution $p_R(r)$ generated by the receiving coil, may be acquired from the above-mentioned process. $p_R(r)$ may also be obtained by a method such as an actual measurement method, an analytical equation solution method or a finite element numerical simulation method.

An excitation current $I_E(t)$ is introduced into the excitation coil to generate a required non-uniform excitation field in an imaging space, so as to excite a magnetic nanoparticle in a space. However, a distribution of the excitation field is not limited and is determined by a geometric structure of the excitation coil itself. The method of the present disclosure may be applied to any excitation coil.

In the step S30, a normalization processing is performed on the response voltage signal $u_p(t)$ so as to obtain a normalized magnetic nanoparticle signal s(t). The normalized magnetic nanoparticle signal s(t) is shown in equation (2).

$$s(t)=u_p(t)/[I_E(t)]^k \qquad (2)$$

Where k is a frequency multiplication number of the response voltage signal $u_p(t)$ of the magnetic nanoparticle, and k is a positive odd number.

The response voltage signal $u_p(t)$ may be a full-band signal, or may be any odd frequency multiplication component, such as one frequency multiplication, three frequency multiplications, five frequency multiplications, etc. The response voltage signal $u_p(t)$ may be selected according to an actual magnetic field strength and a signal-to-noise ratio. k represents the frequency multiplication number and may be selected from 1, 3, 5, etc.

In the step S40, a gridding processing is performed on an imaging space of the to-be-reconstructed object, so as to obtain N imaging subunits, a n-th imaging subunit has a volume $\Delta V_n$ and n=1, 2, ..., N.

For different imaging spaces, the divided imaging subunits are respectively: for a three-dimensional imaging space, the imaging subunit is a voxel; for a two-dimensional imaging space, the imaging subunit is a surface element; for a one-dimensional imaging space, the imaging subunit is a line element.

In the step S50, a normalized signal peak $s_p$ is calculated based on the normalized magnetic nanoparticle signal s(t), and a first mathematical model between the normalized signal peak $s_p$ and the magnetic nanoparticle spatial distribution $c(r_n)$ is constructed by combining the volume $\Delta V_n$ of the imaging subunit. The first mathematical model is shown in equation (3).

$$s_p = \gamma \sum_{n=1}^{N} [A_0(r_n)]^k p_R(r_n) c(r_n) \Delta V_n \qquad (3)$$

Where $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, ..., N and n represents the n-th imaging subunit of N imaging subunits, and γ represents a proportionality constant related to a frequency of an excitation field, a magnetic moment of a single magnetic particle and a temperature.

Presetting that the proportionality constant γ is related to the frequency of the excitation field, the magnetic moment of the single magnetic particle and the temperature, when the above-mentioned parameters remain unchanged, γ is a fixed value; and when the excitation coil, a geometry of the receive coil and a gridding mode are determined, equation parameters $A_0(r_n)$ $p_R(r_n)$ and $\Delta V_n$ are also uniquely determined. k represents a frequency multiplication number and may be 1, 3, 5, etc.

In the step S60, the first mathematical model is solved to obtain the magnetic nanoparticle spatial distribution $c(r_n)$, so as to achieve the magnetic nanoparticle imaging of the to-be-reconstructed object.

In order to improve an imaging accuracy and a spatial resolution, as much data as possible, i.e., more normalized signal peaks $s_p$, need to be acquired. The present disclosure provides both a second embodiment and a third embodiment on the basis of the first embodiment in order to increase the number of $s_p$.

In the second embodiment of the present disclosure, a spatialtemporally coded non-uniform excitation field-based method for performing a magnetic nanoparticle imaging is provided, which includes step A10 to step A60.

Figure 2:
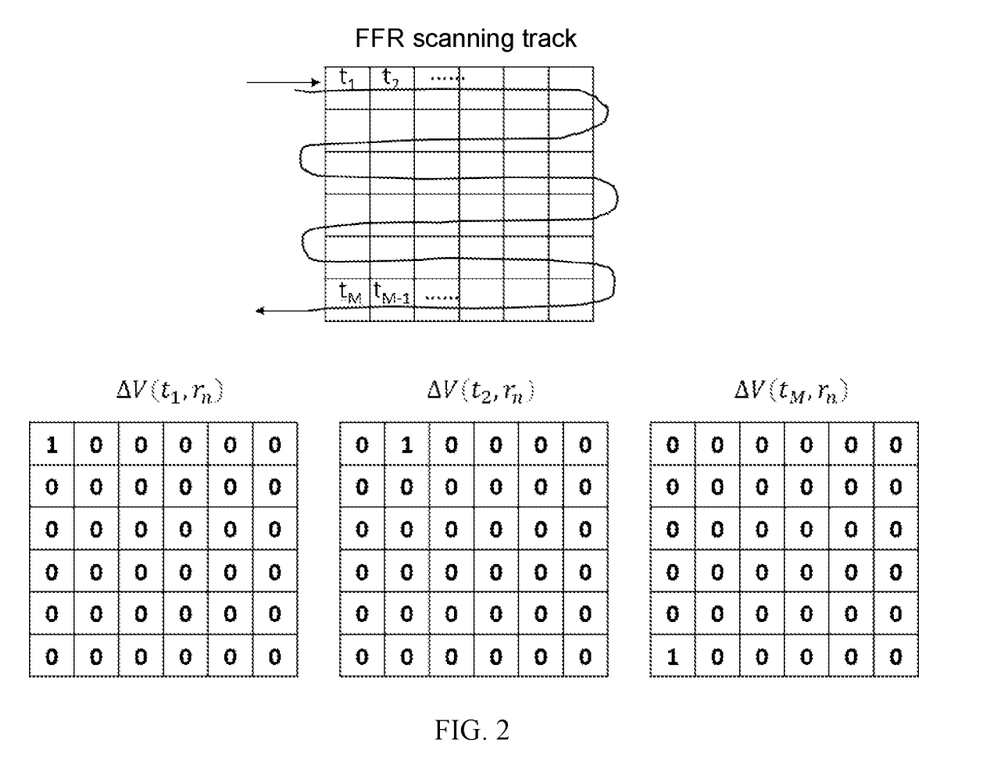
FIG. 2 shows a scanning track schematic diagram of a spatialtemporally coded non-uniform excitation field-based method for performing a magnetic nanoparticle imaging according to an embodiment of the present disclosure.

In the step A10, on the basis of exciting a to-be-reconstructed object through a non-uniform excitation field $H_E(r, t)$ of the non-uniform excitation field-based method for performing a magnetic nanoparticle imaging, a pair of direct current coils in an opposite axial direction or a permanent magnet is additionally added, so as to generate a gradient magnetic field with a field-free region (FFR) in an imaging space. A magnetic nanoparticle in a region outside the FFR is in a saturation state due to a large magnetic field, and may not respond to the excitation field.

In the step A20, a low-frequency alternating magnetic field is generated by a low-frequency alternating current coil and a distribution of the gradient magnetic field is changed, thereby changing a position of the FFR. The FFR is driven to scan and traverse an entire imaging space along a specific track. Each scanning moment corresponds to a certain position in the space, so that M scanning moments and M scanning positions may be obtained.

In the step A30, a normalized signal peak $s_p(t_m)$ is acquired at a m-th moment through the step S10 to step S50 of the above-mentioned non-uniform excitation field-based method for performing a magnetic nanoparticle imaging, where m=1, 2, ..., M.

In the step A40, a voxel function $\Delta V(t_m, r_p)$ of a response voltage signal of a n-th imaging subunit at a m-th scanning moment is acquired according to the distribution of the gradient magnetic field and the scanned track, and a volume of a voxel other than the FFR is set to be zero.

In the step A50, a second mathematical model between the normalized signal peak $s_p(t_m)$ and a magnetic nanoparticle spatial distribution $c(r_n)$ is constructed based on the normalized signal peak $s_p(t_m)$ at the m-th moment and the voxel function $\Delta V(t_m, r_n)$ of the response voltage signal at the m-th scanning moment. The second mathematical model is shown in equation (4).

$$s_p(t_m) = \gamma \sum_{n=1}^{N} [A_0(r_n)]^k p_R(r_n) c(r_n) \Delta V(t_m, r_n) \qquad (4)$$

Where $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, ..., N represents the n-th imaging subunit of N imaging subunits, and γ represents a proportionality constant related to a frequency of an excitation field, a magnetic moment of a single magnetic particle and a temperature.

In the step A60, the second mathematical model is solved to obtain the magnetic nanoparticle spatial distribution $c(r_n)$, so as to achieve the magnetic nanoparticle imaging of the to-be-reconstructed object.

FIG. 2 shows a scanning track schematic diagram of a spatialtemporally coded non-uniform excitation field-based method for performing a magnetic nanoparticle imaging according to an embodiment of the present disclosure. The FFR scans from left to right along a first line, scans from right to left along a second line, scans from left to right along a third line, . . . , and so on, so as to complete the scanning in an entire region. The scanning track is only one preferred track of the present disclosure. In other applications, other scanning tracks may be selected according to actual needs, which will not be described in detail in the present disclosure.

In the third embodiment of the present disclosure, a non-uniform excitation field of a coil array-based method for performing a magnetic nanoparticle imaging is provided, which includes step B10 to step B50.

Figure 3:
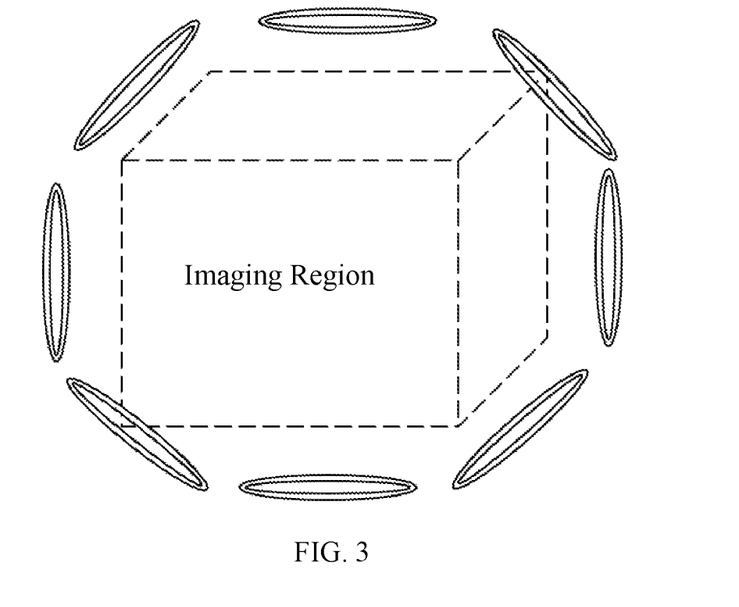
FIG. 3 shows a coil array schematic diagram of a non-uniform excitation field of a coil array-based method for performing a magnetic nanoparticle imaging according to an embodiment of the present disclosure.

In the step B10, on the basis of exciting a to-be-reconstructed object through a non-uniform excitation field in the above-mentioned non-uniform excitation field-based method for performing a magnetic nanoparticle imaging, an imaging space is sequentially excited by using a plurality of excitation coils with same or different axial directions at different positions so as to construct an excitation coil array.

In the step B20, a magnetic nanoparticle response voltage signal is simultaneously detected by using a plurality of receiving coils with same or different axial directions at different positions so as to construct a receiving coil array, and the plurality of receiving coils correspond to the plurality of excitation coils.

In the step B30, through the step S10 to step S50 of the above-mentioned non-uniform excitation field-based method for performing a magnetic nanoparticle imaging, a unit current magnetic field spatial function $A_0^m(r_n)$ of a m-th excitation coil and a sensitivity spatial function $p_R^l(r_n)$ of a l-th receiving coil is acquired, a volume $\Delta V_n$ of a n-th imaging subunit is acquired and n=1, 2, . . . , N, a normalization of a m×l magnetic nanoparticle response voltage signal is performed, and a normalized signal peak $s_p^{m \times l}$ of a normalized magnetic nanoparticle signal s(t) is acquired.

In the step B40, a third mathematical model between the normalized signal peak $s_p^{m \times l}$ and a magnetic nanoparticle spatial distribution $c(r_n)$ is constructed based on the normalized signal peak $s_p^{m \times l}$ and the volume $\Delta V_n$ of the imaging subunit. The third mathematical model is shown in equation (5).

$$s_p^{m \times l} = \gamma \sum_{n=1}^{N} [A_0^m(r_n)]^k p_R^l(r_n) c(r_n) \Delta V_n \quad (5)$$

Where $A_0(r_n)$ represents a spatial distribution of a non-uniform magnetic field generated by an excitation coil corresponding to a n-th imaging subunit, $p_R(r_n)$ represents a magnetic field spatial distribution generated by a receiving coil corresponding to the n-th imaging subunit, n=1, 2, . . . , N represents the n-th imaging subunit of N imaging subunits, γ represents a proportionality constant related to a frequency of an excitation field, a magnetic moment of a single magnetic particle and a temperature, m represents the m-th excitation coil, and l represents the l-th receiving coil.

In the step B50, the third mathematical model is solved to obtain the magnetic nanoparticle spatial distribution, so as to achieve the magnetic nanoparticle imaging of the to-be-reconstructed object.

FIG. 3 shows a coil array schematic diagram of a non-uniform excitation field of a coil array-based method for performing a magnetic nanoparticle imaging according to an embodiment of the present disclosure. The coil array includes an excitation coil and a receiving coil. A circle of coils outside an imaging region is a schematic diagram of the coil array, which indicates a presence of a plurality of excitation coils or receiving coils at different axes. Positions of the excitation coils and positions of the receiving coils are not particularly limited, and may be flexibly adjusted as needed in practical applications, which is not described in detail in the present disclosure.

Although the above-mentioned embodiments have described the steps in the above-mentioned sequence, those skilled in the art will appreciate that, in order to achieve the effect of this embodiment, different steps are not necessarily performed in such a sequence, and may be performed simultaneously (in parallel) or in an inverse sequence. These simple variations are all within the scope of protection of the present disclosure.

In the fourth embodiment of the present disclosure, a non-uniform excitation field-based system for performing a magnetic nanoparticle imaging is provided, and the system, based on the above-mentioned non-uniform excitation field-based method for performing a magnetic nanoparticle imaging, includes:
   a first magnetic field excitation module configured to excite a to-be-reconstructed object through a non-uniform excitation field $H_E(r, t)$;
   a spatialtemporal separation module configured to perform a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;
   a magnetic field spatial distribution and response voltage signal acquisition module configured to acquire, based on the spatial distribution $A_0(r)$ of the non-uniform magnetic field generated by the excitation coil and the excitation current time-domain waveform $I_E(t)$ a magnetic field space distribution $p_R(r)$ generated by a receiving coil and a magnetic nanoparticle response voltage signal $u_p(t)$;
   a normalization module configured to perform a normalization processing on the magnetic nanoparticle response voltage signal $u_p(t)$, so as to obtain a normalized magnetic nanoparticle signal s(t);
   a gridding module configured to perform a gridding processing on an imaging space of the to-be-reconstructed object, so as to obtain N imaging subunits, wherein a n-th imaging subunit has a volume $\Delta V_n$ and n=1, 2, . . . , N;
   a first model construction module configured to calculate a normalized signal peak $s_p$ based on the normalized magnetic nanoparticle signal s(t) and to construct a first mathematical model between the normalized signal peak $s_p$ and the magnetic nanoparticle spatial distribution $c(r_n)$ by combining the volume $\Delta V_n$ of the imaging subunit; and
   a first imaging module configured to solve the first mathematical model to obtain the magnetic nanoparticle spatial distribution $c(r_n)$, so as to achieve the magnetic nanoparticle imaging of the to-be-reconstructed object.

In the fifth embodiment of the present disclosure, a spatialtemporally coded non-uniform excitation field-based system for performing a magnetic nanoparticle imaging is provided. Based on the above-mentioned non-uniform excitation field-based method for performing a magnetic nanoparticle imaging and the above-mentioned spatialtemporally coded non-uniform excitation field-based method for performing a magnetic nanoparticle imaging, the system includes the following modules for performing corresponding operations.

A second magnetic field excitation module is configured to generate, on the basis of exciting a to-be-reconstructed object through a non-uniform excitation field $H_E(r, t)$, a gradient magnetic field with a field-free region in an imaging space through a pair of direct current coils in an opposite axial direction or a permanent magnet.

A scanning module is configured to change a distribution of the gradient magnetic field through a low-frequency alternating magnetic field generated by a low-frequency alternating current coil, and to drive the field-free region to scan and traverse an entire imaging space along a set track, so as to obtain M scanning moments and M scanning positions.

A first normalized signal peak acquisition module is configured to acquire a normalized signal peak $s_p(t_m)$ at a m-th moment through step S10 to step S50 of the above-mentioned non-uniform excitation field-based method for performing a magnetic nanoparticle imaging, wherein m=1, 2, . . . , M.

A voxel function generation module is configured to acquire a voxel function $\Delta V(t_m, r_n)$ of a response voltage signal of a n-th imaging subunit at a m-th scanning moment according to the distribution of the gradient magnetic field and the scanned track.

A second mathematical model construction module is configured to construct a second mathematical model between the normalized signal peak $s_p(t_m)$ and a magnetic nanoparticle spatial distribution $c(r_n)$ based on the normalized signal peak $s_p(t_m)$ at the m-th moment and the voxel function $\Delta V(t_m, r_n)$ of the response voltage signal at the m-th scanning moment.

A second imaging module is configured to solve the second mathematical model to obtain the magnetic nanoparticle spatial distribution $c(r_n)$, so as to achieve the magnetic nanoparticle imaging of the to-be-reconstructed object.

In the sixth embodiment of the present disclosure, a non-uniform excitation field of a coil array-based system for performing a magnetic nanoparticle imaging is provided. Based on the above-mentioned non-uniform excitation field-based method for performing a magnetic nanoparticle imaging and the above-mentioned non-uniform excitation field of a coil array-based method for performing a magnetic nanoparticle imaging, the system includes the following modules for performing corresponding operations.

A third magnetic field excitation module is configured to sequentially excite, on the basis of exciting a to-be-reconstructed object through a non-uniform excitation field $H_E(r, t)$, an imaging space by using a plurality of excitation coils with same or different axial directions at different positions so as to construct an excitation coil array, and to simultaneously detect a magnetic nanoparticle response voltage signal by using a plurality of receiving coils with same or different axial directions at different positions so as to construct a receiving coil array, and the plurality of receiving coils correspond to the plurality of excitation coils.

A second normalized signal peak acquisition module is configured to acquire a unit current magnetic field spatial function $A_0^m(r_n)$ of a m-th excitation coil and a sensitivity spatial function $p_R^l(r_n)$ of a l-th receiving coil, acquire a volume $\Delta V_n$, n=1, 2, . . . , N of a n-th imaging subunit, perform a normalization of a m×l magnetic nanoparticle response voltage signal, and acquire a normalized signal peak $s_p^{m \times l}$ of a normalized magnetic nanoparticle signal s(t) through step S10 to step S50 of the above-mentioned non-uniform excitation field-based method for performing a magnetic nanoparticle imaging.

A third mathematical model construction module is configured to construct a third mathematical model between the normalized signal peak $s_p^{m \times l}$ and a magnetic nanoparticle spatial distribution $c(r_n)$ based on the normalized signal peak $s_p^{m \times l}$ and the volume $\Delta V_n$ of the imaging subunit.

A third imaging module is configured to solve the third mathematical model to obtain the magnetic nanoparticle spatial distribution $c(r_n)$, so as to achieve the magnetic nanoparticle imaging of the to-be-reconstructed object.

Those skilled in the art will clearly understand that, for convenience and simplicity of description, the specific working process and related description of the above-mentioned system may be explained with reference to the corresponding process in the method embodiment described above, which will not repeated here.

It should be noted that the non-uniform excitation field-based system of performing a magnetic nanoparticle imaging, the spatialtemporally coded non-uniform excitation field-based system of performing a magnetic nanoparticle imaging and the non-uniform excitation field of a coil array-based system of performing a magnetic nanoparticle imaging provided in the above-mentioned embodiments are only illustrated by a division of the above-mentioned functional modules. In practical applications, an allocation of the above-mentioned functions may be completed by different functional modules as needed, that is, the modules or steps in the embodiments of the present disclosure are further decomposed or combined. For example, the modules in the above-mentioned embodiments may be combined into a module, or may be further split into a plurality of sub-modules, so as to complete all or part of the functions described above. Names of the modules and steps involved in the embodiments of the present disclosure are only to distinguish each modules or step, and are not to be regarded as an improper limitation on the present disclosure.

In the seventh embodiment of the present disclosure, there is provided an electronic device including:
at least one processor; and
a memory in communication with the at least one processor.

The memory has an instruction executable by the processor stored therein, and the instruction is used to be executed by the processor so as to implement the above-mentioned non-uniform excitation field-based method for performing a magnetic nanoparticle imaging, or the above-mentioned spatialtemporally coded non-uniform excitation field-based method for performing a magnetic nanoparticle imaging, or the above-mentioned non-uniform excitation field of a coil array-based method for performing a magnetic nanoparticle imaging.

In the eighth embodiment of the present disclosure, there is provided a computer-readable storage medium, the computer-readable storage medium has a computer instruction executable by the computer so as to implement the above-mentioned non-uniform excitation field-based method for performing a magnetic nanoparticle imaging, or the above-mentioned spatialtemporally coded non-uniform excitation field-based method for performing a magnetic nanoparticle imaging, or the above-mentioned non-uniform excitation field of a coil array-based method for performing a magnetic nanoparticle imaging.

Beneficial Effects of the Present Disclosure

The non-uniform excitation field-based method for performing a magnetic nanoparticle imaging in the present disclosure includes: exciting the magnetic nanoparticle by using the non-uniform excitation field so as to generate a non-uniform response voltage signal, separating the non-uniform excitation field into an independent spatial function and a current time function by a spatialtemporal separation method, calculating a normalized signal peak by the current time function, and finally quantitatively reconstructing a spatial distribution of a nanoparticle by combining the normalized signal peak, a non-uniform spatial function of an excitation field and a reconstruction equation. The method of the present disclosure may solve problems such as a large power consumption, a high maintenance cost, a difficulty in generating a wide-range uniform high-frequency excitation field and the like caused by a necessary use of a uniform excitation field in a traditional method for performing a magnetic nanoparticle imaging. At the same time, the method may reduce an artifact error caused by the non-uniform excitation field, and effectively improve a precision and a resolution of an image.

Those skilled in the art will clearly understand that, for convenience and simplicity of description, the specific working process and related descriptions of the storage device and the processing device described above may be explained with reference to the corresponding process in the method embodiment described above, which will not repeated here.

Those skilled in the art will appreciate that modules and method steps of each example described in conjunction with the embodiments disclosed herein may be implemented by an electronic hardware, a computer software, or a combinations thereof. Programs corresponding to software modules and method steps may be placed in a random access memory (RAM), a memory, a read only memory (ROM), an electrically programmable ROM, an electrically erasable programmable ROM, a register, a hard disk, a removable disk, a CD-ROM, or any other form of storage medium known in the art. In order to clearly illustrate an interchangeability between an electronic hardware and an electronic software, components and steps of each example have been generally described above in terms of their functionality. Whether these functions are performed by the electronic hardware or the electronic software depends on the particular application and design constraint of the technical solution. Those skilled in the art may implement the function described above using different methods for each particular application, but such implementation should not be considered beyond the scope of the present disclosure.

The terms such as "first," "second," and the like are used to distinguish between similar elements and not necessarily to describe or imply a particular order or sequence.

The terms "including," or any other variation thereof, are intended to cover a non-exclusive inclusion, so that a process, a method, an article or a device/apparatus including a list of elements include not only those elements, but also other elements not expressly listed, or elements inherent to the process, the method, the article or the device/apparatus.

So far, the technical solution of the present disclosure has been described in conjunction with the embodiments shown in the accompanying drawings. However, those skilled in the art may easily understand that the scope of protection of the present disclosure is obviously not limited to these specific embodiments. Without departing from the principle of the present disclosure, those skilled in the art may make equivalent changes or substitutions of related technical features, and these technical solutions to be changed or substituted should all fall within the scope of protection of the present disclosure.

What is claimed is:

1. A non-uniform excitation field-based method for performing a magnetic nanoparticle imaging, comprising:
   exciting a to-be-reconstructed object through a non-uniform excitation field $H_E(r, t)$, and performing a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;
   acquiring, based on the spatial distribution $A_0(r)$ of the non-uniform magnetic field generated by the excitation coil and the excitation current time-domain waveform $I_E(t)$, a magnetic field space distribution $p_R(r)$ generated by a receiving coil and a magnetic nanoparticle response voltage signal $u_p(t)$;
   performing a normalization processing on the magnetic nanoparticle response voltage signal $u_p(t)$, so as to obtain a normalized magnetic nanoparticle signal $s(t)$;
   performing a gridding processing on an imaging space of the to-be-reconstructed object, so as to obtain N imaging subunits, wherein a n-th imaging subunit has a volume $\Delta V_n$ and n=1, 2, ..., N;
   calculating a normalized signal peak $s_p$ based on the normalized magnetic nanoparticle signal $s(t)$, and constructing a first mathematical model between the normalized signal peak $s_p$ and a magnetic nanoparticle spatial distribution $c(r_n)$ by combining the volume $\Delta V_n$ of the imaging subunit; and
   solving the first mathematical model to obtain the magnetic nanoparticle spatial distribution $c(r_n)$, so as to achieve the magnetic nanoparticle imaging of the to-be-reconstructed object.

2. The method according to claim 1, wherein the excitation current time-domain waveform $A_0(r)$ of the non-uniform magnetic field generated by the excitation coil and the magnetic field space distribution $p_R(r)$ generated by the receiving coil are acquired by one of an actual measurement method, an analytical equation solution method or a finite element numerical simulation method, respectively.

3. The method according to claim 1, wherein the excitation current time-domain waveform $I_E(t)$ is one of a sine wave, a cosine wave, a square wave or a pulse wave.

4. The method according to claim 1, wherein the normalized magnetic nanoparticle signal $s(t)$ is acquired by:

$$s(t)=u_p(t)/[I_E(t)]^k$$

wherein k is a frequency multiplication number of the magnetic nanoparticle response voltage signal $u_p(t)$, and k is a positive odd number.

5. The method according to claim 4, wherein the first mathematical model between the normalized signal peak $s_p$ and the magnetic nanoparticle spatial distribution $c(r_n)$ is expressed as:

$$s_p = \gamma \sum_{n=1}^{N} [A_0(r_n)]^k p_R(r_n) c(r_n) \Delta V_n$$

wherein $A_0(r_n)$ represents the spatial distribution of a non-uniform magnetic field generated by the excitation coil corresponding to a n-th imaging subunit, $p_R(r_n)$ represents a magnetic field spatial distribution generated by the receiving coil corresponding to the n-th imaging subunit, n=1, 2, ..., N and n represents the n-th imaging subunit of N imaging subunits, and $\gamma$ represents a proportionality constant related to a frequency of an excitation field, a magnetic moment of a single magnetic particle and a temperature.

6. A spatialtemporally coded non-uniform excitation field-based method for performing a magnetic nanoparticle imaging, comprising:

generating, on the basis of exciting a to-be-reconstructed object through a non-uniform excitation field $H_E(r, t)$ of the method according to claim 1, a gradient magnetic field with a field-free region in an imaging space through a pair of direct current coils in an opposite axial direction or a permanent magnet;

changing a distribution of the gradient magnetic field through a low-frequency alternating magnetic field generated by a low-frequency alternating current coil, and driving the field-free region to scan and traverse an entire imaging space along a set track, so as to obtain M scanning moments and M scanning positions;

acquiring a normalized signal peak $s_p(t_m)$ at a m-th moment thorough the method according to claim 1, wherein m=1, 2, . . . , M;

acquiring a voxel function $\Delta V(t_m, r_n)$ of a response voltage signal of a n-th imaging subunit at a m-th scanning moment according to the distribution of the gradient magnetic field and the scanned track;

constructing a second mathematical model between the normalized signal peak $s_p(t_m)$ and a magnetic nanoparticle spatial distribution $c(r_n)$ based on the normalized signal peak $s_p(t_m)$ at the m-th moment and the voxel function $\Delta V(t_m, r_n)$ of the response voltage signal at the m-th scanning moment; and solving the second mathematical model to obtain the magnetic nanoparticle spatial distribution $c(r_n)$, so as to achieve the magnetic nanoparticle imaging of the to-be-reconstructed object.

7. The method according to claim 6, wherein the second mathematical model between the normalized signal peak $s_p(t_m)$ and the magnetic nanoparticle spatial distribution $c(r_n)$ is expressed as:

$$s_p(t_m) = \gamma \sum_{n=1}^{N} [A_0(r_n)]^k p_R(r_n) c(r_n) \Delta V(t_m, r_n)$$

wherein $A_0(r_n)$ represents the spatial distribution of a non-uniform magnetic field generated by the excitation coil corresponding to a n-th imaging subunit, k represents a frequency multiplication number of the magnetic nanoparticle response voltage signal and k is a positive odd number, $p_R(r_n)$ represents a magnetic field spatial distribution generated by the receiving coil corresponding to the n-th imaging subunit, n=1, 2, . . . , N and n represents the n-th imaging subunit of N imaging subunits, $\gamma$ represents a proportionality constant related to a frequency of an excitation field, a magnetic moment of a single magnetic particle and a temperature, and $t_m$ represents the m-th scanning moment.

8. A non-uniform excitation field of a coil array-based method for performing a magnetic nanoparticle imaging, comprising:

sequentially exciting, on the basis of exciting a to-be-reconstructed object through a non-uniform excitation field $H_E(r, t)$ of the method according to claim 1, an imaging space by using a plurality of excitation coils with same or different axial directions at different positions, so as to construct an excitation coil array;

simultaneously detecting a magnetic nanoparticle response voltage signal by using a plurality of receiving coils with same or different axial directions at different positions so as to construct a receiving coil array, wherein the plurality of receiving coils correspond to the plurality of excitation coils;

acquiring a unit current magnetic field spatial function $A_0^m(r_n)$ of a m-th excitation coil and a sensitivity spatial function $p_R^l(r_n)$ of a l-th receiving coil, acquiring a volume $\Delta V_n$ of a n-th imaging subunit and n=1, 2, . . . , N, performing a normalization of a m×l magnetic nanoparticle response voltage signal $u_p(t)$, and acquiring a normalized signal peak $s_p^{m \times l}$ of a normalized magnetic nanoparticle signal $s(t)$ through the method according to claim 1;

constructing a third mathematical model between the normalized signal peak $s_p^{m \times l}$ and a magnetic nanoparticle spatial distribution $c(r_n)$ based on the normalized signal peak $s_p^{m \times l}$ and the volume $\Delta V_n$ of the imaging subunit; and solving the third mathematical model to acquire the magnetic nanoparticle spatial distribution $c(r_n)$, so as to achieve the magnetic nanoparticle imaging of the to-be-reconstructed object.

9. The method according to claim 8, wherein the third mathematical model between the normalized signal peak $s_p^{m \times l}$ and the magnetic nanoparticle spatial distribution $c(r_n)$ is expressed as:

$$s_p^{m \times l} = \gamma \sum_{n=1}^{N} [A_0^m(r_n)]^k p_R^l(r_n) c(r_n) \Delta V_n$$

wherein $A_0(r_n)$ represents the spatial distribution of a non-uniform magnetic field generated by the excitation coil corresponding to a n-th imaging subunit, k represents a frequency multiplication number of the magnetic nanoparticle response voltage signal and k is a positive odd number, $p_R(r_n)$ represents a magnetic field spatial distribution generated by the receiving coil corresponding to the n-th imaging subunit, n=1, 2, . . . , N and n represents the n-th imaging subunit of N imaging subunits, $\gamma$ represents a proportionality constant related to a frequency of an excitation field, a magnetic moment of a single magnetic particle and a temperature, m represents the m-th excitation coil and l represents the l-th receiving coil.

10. A non-uniform excitation field-based system for performing a magnetic nanoparticle imaging, the system, based on the method according to claim 1, comprising:

a first magnetic field excitation module configured to excite a to-be-reconstructed object through a non-uniform excitation field $H_E(r, t)$;

a spatialtemporal separation module configured to perform a spatialtemporal separation of the non-uniform excitation field $H_E(r, t)$, so as to obtain a spatial distribution $A_0(r)$ of a non-uniform magnetic field generated by an excitation coil and an excitation current time-domain waveform $I_E(t)$;

a magnetic field spatial distribution and response voltage signal acquisition module configured to acquire, based on the spatial distribution $A_0(r)$ of the non-uniform magnetic field generated by the excitation coil and the excitation current time-domain waveform $I_E(t)$, a magnetic field space distribution $p_R(r)$ generated by a receiving coil and a magnetic nanoparticle response voltage signal $u_p(t)$;

a normalization module configured to perform a normalization processing on the magnetic nanoparticle response voltage signal $u_p(t)$, so as to obtain a normalized magnetic nanoparticle signal $s(t)$;

a gridding module configured to perform a gridding processing on an imaging space of the to-be-reconstructed object, so as to obtain N imaging subunits, wherein a n-th imaging subunit has a volume $\Delta V_n$ and n=1, 2, . . . , N;

a first model construction module configured to calculate a normalized signal peak $s_p$ based on the normalized magnetic nanoparticle signal $s(t)$ and to construct a first mathematical model between the normalized signal peak $s_p$ and the magnetic nanoparticle spatial distribution $c(r_n)$ by combining the volume $\Delta V_n$ of the imaging subunit; and a first imaging module configured to solve the first mathematical model to obtain the magnetic nanoparticle spatial distribution $c(r_n)$, so as to achieve the magnetic nanoparticle imaging of the to-be-reconstructed object.

* * * * *